United States Patent [19]

Langer

[11] Patent Number: 4,791,119
[45] Date of Patent: Dec. 13, 1988

[54] PHARMACEUTICAL COMPOSITION FOR TREATMENT OF OBESITY

[75] Inventor: Salomon Langer, Paris, France

[73] Assignee: Synthelabo, Paris, France

[21] Appl. No.: 94,430

[22] Filed: Sep. 9, 1987

[30] Foreign Application Priority Data

Sep. 10, 1986 [FR] France ............................ 8612642

[51] Int. Cl.⁴ .......................................... A61K 31/445
[52] U.S. Cl. ..................................... 514/317; 514/910
[58] Field of Search ............................. 514/319, 910

[56] References Cited

U.S. PATENT DOCUMENTS 4,443,462  4/1984  Carr et al. ........................... 514/319
4,529,730  7/1985  Schneider et al. ................... 514/319

OTHER PUBLICATIONS

Chem Abst. 99:105130q (1983)–Schneider et al.
Chem. Abst. 99:158258n (1983)–Schneider et al.
Chem. Abst. 99:158270s (1983)–Schneider et al.
Chem. Abst. 99:88062z (1983)–Synthelado.
Chem. Abst. 105:172295c (1986)–Synthelado.

Primary Examiner—Douglas W. Robinson
Attorney, Agent, or Firm—Wegner & Bretschneider

[57] ABSTRACT

A method of treatment of obesity which comprises administering to a subject liable thereto or suffering therefrom an effective dose of 4-(2-naphthylmethoxy)-piperidine.

2 Claims, No Drawings

PHARMACEUTICAL COMPOSITION FOR TREATMENT OF OBESITY

The present invention relates to pharmaceutical compositions.

4-(2-naphthylmethoxy)piperidine is described in French Patent of Addition No. 81/19,025 (2,514,353) dated Oct. 9, 1981, to Pat. No. 80/09,513, as having antidepressant properties.

We have suprisingly found, according to the present invention, that 4-(2-naphthylmethoxy)piperidine possesses anorexigenic properties and that it may therefore be employed in the treatment of obesity.

The present invention provides the use of 4-(2-naphthylmethoxy)piperidine in the manufacture of a medicament for the treatment or prevention of obesity.

The present invention also provides a method of treatment of obesity which comprises administering to a subject liable thereto or suffering therefrom an effective dose of 4-(2-naphthylmethoxy)piperidine.

4-(2-naphthylmethoxy)piperidine has the formula:

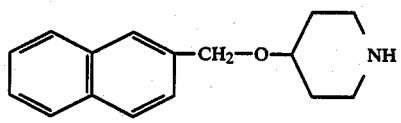

It may be prepared as described in the abovementioned document by reacting 2-naphthylmethyl chloride and 4-hydroxy-4-nitro-1-benzoylpiperidine, followed by the deprotection of the nitrogen in the piperidine group. 4-(2-naphthylmethoxy)piperidine fumarate melts at 170°–171.5° C.

The following Example further illustrates the present invention.

EXAMPLE 1

The following pharmacological trials were carried out:

Male Sprague-Dawley rats (Charles river, France) weighing 210 to 250 g were maintained in a light/dark atmosphere based on a 12 hour cycle. They were supplied with water throughout the period of the experiment.

Before the trials, the rats were starved for 18 to 20 hours. All the trials started at approximately 9.00 am–10.00 am.

4-(2-naphthylmethoxy)piperidine (1 ml/kg) was dissolved in saline and administered to the rats by injection or force-feeding. The animals were placed in plastic cages into which food was introduced in previously weighed Petri dishes 5, 10 or 30 min after the administration of the compound of interest.

At constant intervals (0.5 h), the food containers were withdrawn and the quantity of food remaining was weighed. The significance of the data was anzalysed by Duncan or Dunnett tests.

At doses of 1 to 10 mg/kg by the intraperitoneal route, the compound produced an inhibition of food intake, depending on the dose, during the first hour following the introduction of food.

The maximum anorexigenic effect was obtained within the first 30 to 60 minutes following the introduction of food.

The AD50 (dose which inhibits 50% of food intake during the first 30 minutes) of the compound was 3.8 mg/kg by the intraperitoneal route.

When the compound was administered by the oral route, a marked inhibition of food intake was observed at doses of 5 to 30 mg/kg.

4-(2-naphthylmethoxy)piperidine thus is shown to be a relatively strong anorexigenic agent, and can therefore be usen in the treatment of obesity.

Pharmaceutical compositions containing the compound in combination with any excipient suitable for oral or parenteral administration form part of the invention.

The daily dose typically ranges from 10 to 50 mg.

I claim:

1. A method of treatment of obesity which comprises administering to a subject in need thereof an effective anorectic amount of 4-(2-naphthylmethoxy)piperidine.

2. A method according to claim 1 wherein the daily dose is from 10 to 50 mg.

* * * * *